US011446403B2

(12) United States Patent
Duncan et al.

(10) Patent No.: US 11,446,403 B2
(45) Date of Patent: Sep. 20, 2022

(54) AUTOMATIC FAR-UV ENVIRONMENTAL SANITIZATION

(71) Applicant: UVDevelopment LLC, Needham, MA (US)

(72) Inventors: Francis P Duncan, Needham, MA (US); Kevin T Arthur, Medfield, MA (US)

(73) Assignee: UVDEVELOPMENT LLC, Needham, MA (US)

( * ) Notice: Subject to any disclaimer, the term of this patent is extended or adjusted under 35 U.S.C. 154(b) by 0 days.

(21) Appl. No.: 17/397,721

(22) Filed: Aug. 9, 2021

(65) Prior Publication Data

US 2022/0054675 A1 Feb. 24, 2022

Related U.S. Application Data

(60) Provisional application No. 63/123,638, filed on Dec. 10, 2020, provisional application No. 63/067,054, filed on Aug. 18, 2020.

(51) Int. Cl.
*A61L 2/10* (2006.01)
*A61L 2/24* (2006.01)

(52) U.S. Cl.
CPC ................... *A61L 2/10* (2013.01); *A61L 2/24* (2013.01); *A61L 2202/14* (2013.01)

(58) Field of Classification Search
CPC .......... A61L 2/10; A61L 2/24; A61L 2202/14
See application file for complete search history.

(56) References Cited

U.S. PATENT DOCUMENTS

| 2015/0343104 | A1* | 12/2015 | Maxik | ....................... G01J 1/42 250/201.1 |
| 2020/0147249 | A1* | 5/2020 | Hussein | .................... A61L 2/24 |
| 2020/0345875 | A1* | 11/2020 | Trapani | ............... H01M 10/425 |

* cited by examiner

*Primary Examiner* — Sean E Conley
(74) *Attorney, Agent, or Firm* — Nixon Peabody LLP

(57) ABSTRACT

A system using a Far-UV light source is disclosed for sanitizing an environment. The light source can be automatically activated based on environment dimension information, environment usage information, light source specification information, and/or regulatory compliance information. Activation of the light source can be further based on sensor data from the environment, such as occupancy sensor data. The controller can further monitor and log light source usage, such as to update an expected remaining lifespan of the light source and generate a compliance report of light source usage. Activation of the light source can be further based on the expected remaining lifespan of the light source. When the expected remaining lifespan of the light source drops below a threshold, a maintenance prediction alert can be generated to facilitate maintaining and/or replacing the light source.

20 Claims, 8 Drawing Sheets

AUTOMATIC FAR-UV ENVIRONMENTAL SANITIZATION

CROSS REFERENCE TO RELATED APPLICATIONS

The present application claims the benefit of U.S. Provisional Patent Application No. 63/067,054 filed on Aug. 18, 2020 and entitled "AUTOMATIC FAR-UV ENVIRONMENTAL STERILIZATION," and U.S. Provisional Patent Application No. 63/123,638 filed on Dec. 10, 2020 and entitled "AUTOMATIC FAR-UV ENVIRONMENTAL SANITIZATION," the disclosures of which are hereby incorporated by reference in their entirety.

TECHNICAL FIELD

The present disclosure relates to environmental sanitization techniques generally and more specifically to control systems for UV-light-based sanitization.

BACKGROUND

It is becoming increasingly important to be able to safely and effectively sanitize environments. As experienced during the pandemic related to the severe acute respiratory syndrome coronavirus 2 (SARS-CoV-2 or COVID-19), viruses, like other such pathogens, can collect and remain within environments even after a disease carrier has left the environment. Precautionary measures to prevent exposing healthy individuals to pathogens often include various cleaning and sanitization techniques.

Generally, sanitizing an environment requires the evacuation of the environment for a certain length of time, during which the environment is treated, such as with a sanitization fog or ultraviolet (UV) light. If the environment is used repeatedly or continuously for long periods of time, pathogens can build up to dangerous levels. In such environments, current sanitization techniques may require the environment to be shut down for a period of time for cleaning and sanitization, during which time individuals cannot make use of the environment. Depending on the type of environment, the effects of such downtime can range from inconvenience to loss of business and profits, all the way to harm to individuals and loss of life. In some environments where it may be impossible or impractical to completely shut down the environment for cleaning and sanitization, other time consuming and potentially ineffective sanitization techniques (e.g., manually scrubbing and cleaning of surfaces) are the only available techniques.

UV-light-based sanitization involves application of UV light to damage pathogens and deactivate the deoxyribonucleic acid (DNA) and/or ribonucleic acid (RNA) of pathogens. Some common UV-C type UV sanitization lights operate at or around 254 nm. While this frequency may be useful for sanitization, it can also be harmful to humans. The use of UV sanitization techniques can be especially problematic for use in environments that are regularly or frequently occupied, especially with non-routine occupation schedules. Thus, UV sanitization techniques are often limited to application where risk of human exposure is nonexistent, such as sanitizing enclosed chambers or machinery. In one example, UV sanitization can be limited to enclosed chambers in an heating, ventilation, and air conditioning (HVAC) system, which may be able to sanitize a unit of air, but cannot sanitize surfaces in the occupied environment. Current UV-light-based sanitization techniques are inadequate for automatically and repeatedly sanitizing large environments, especially environments frequented by humans, such as rooms, elevators, vehicles, and the like. There is a need for a safe and effective way to control UV-light-based sanitization.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a method comprising: receiving environmental dimension information associated with an environment; receiving environmental expected usage information associated with the environment; receiving light source specification information associated with a light source in the environment, the light source operable to generate Far-UV light; receiving regulatory compliance information associated with the environment; determining light activation settings for activating the light source based on the environmental dimension information, the environmental expected usage information, the light source specification information, and the regulatory compliance information; and activating the light source based on the determined light activation settings.

In some cases, the method further comprises receiving sensor data, wherein determining the light activation settings is further based on the sensor data. In some cases, the sensor data is associated with the environment. In some cases, the sensor data is associated with the light source. In some cases, the method further comprises logging the activation of the light source. In some cases, the method further comprises generating a compliance report based on the logged activation of the light source. In some cases, the method further comprises determining an expected remaining lifespan of the light source, wherein determining the light activation settings is further based on the determined expected remaining lifespan of the light source. In some cases, the method further comprises generating a maintenance prediction alert associated with the light source, wherein generating the maintenance prediction alert is based on the determined expected remaining lifespan of the light source.

Embodiments of the present disclosure include a system comprising: a control system including one or more processors; and a memory having stored thereon machine readable instructions; wherein the control system is coupled to the memory, and the method disclosed above is implemented when the machine executable instructions in the memory are executed by at least one of the one or more processors of the control system.

Embodiments of the present disclosure include a system for sanitizing an environment, the system including a control system configured to implement the method disclosed above.

Embodiments of the present disclosure include a computer program product comprising instructions which, when executed by a computer, cause the computer to carry out the method disclosed above. In some cases, the computer program product is a non-transitory computer readable medium.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
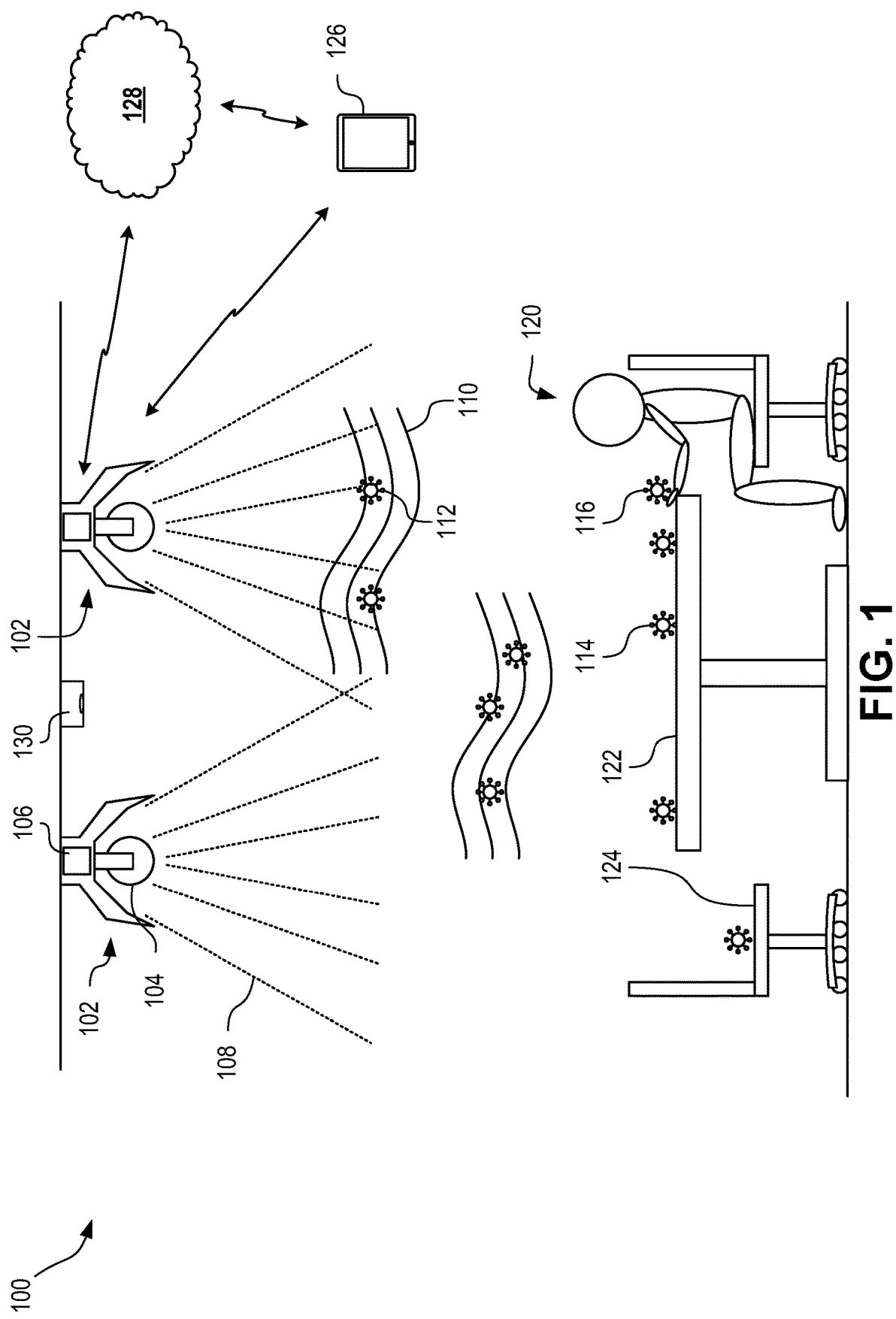
FIG. 1 is a schematic side view of an environment with two Far-UV sanitization devices, according to certain aspects of the present disclosure.

Certain aspects and features of the present disclosure relate to a system for sanitizing an environment using a Far-UV light source. This light source can be automatically controlled by a controller that uses an algorithm to activate the light source at desired times. The controller can activate the light source based on environment dimension information, environment usage information, light source specification information, and/or regulatory compliance information. Activation of the light source can be further based on sensor data from the environment, such as occupancy sensor data. The controller can further monitor and log light source usage, such as to update an expected remaining lifespan of the light source and generate a compliance report of light source usage. Activation of the light source can be further based on the expected remaining lifespan of the light source. When the expected remaining lifespan of the light source drops below a threshold, a maintenance prediction alert can be generated to facilitate maintaining and/or replacing the light source.

Certain aspects and features of the present disclosure are especially useful for treating shared occupied environments, such as vehicles (e.g., ride sharing vehicles and public transportation vehicles), rooms (e.g., conference rooms, classrooms, entry rooms, bathrooms), venues (e.g., restaurants, theatres, waiting rooms), thresholds (e.g., entryways, access control corridors, elevators), shared equipment (e.g., automatic teller machines, shopping carts, restaurant tables), and the like. Certain aspects and features of the present disclosure are suitable for sanitizing both the air and surfaces of an environment.

As used herein, the term environment is inclusive of a space in which the light source is being used. The environment can be a space defined by the reach and/or effective range (e.g., effective for sanitization) of the Far-UV light emitted from the light source and/or a collection of associated light sources. For example, in some cases, an environment can be a small room enclosed by walls. In another example, a very large enclosure, such as a convention room, can include many light sources, in which the convention room can be considered a single large environment with respect to a single system including the many light sources, or can be considered a set of smaller environments (e.g., overlapping or non-overlapping environments) with respect to each individual light source within the convention room. In some cases, an environment may extend beyond walls and/or barriers. In some cases, an environment is inclusive of regions that may not be directly illuminated by the light source, but which may share airflow (e.g., substantial airflow) with regions illuminated by the light source. In an example, a conference room illuminatable by a light source may be considered an environment, even if the light source does not directly illuminate some regions of the room, such as regions blocked by other objects (e.g., regions below a conference table).

In some cases, the term sanitization can refer to sterilization. For example, use of certain aspects and features of the present disclosure to sterilize an environment may include killing, or otherwise rendering unharmful to humans, any pathogens present in the environment. In some cases, however, sanitizing an environment may include killing, or otherwise rendering unharmful to humans, at least a percentage of pathogens present in the environment. As used with respect to UV-light-based sanitization, the term sanitization can include supplying UV-light of a sufficient frequency, power, and duration designed to kill or otherwise render unharmful to humans, a desired percentage of pathogens that may be present in the environment.

Aspects of the present disclosure make use of a Far-UV light source. The Far-UV light source is a light source at or around 222 nm, such as between 100 nm and 230 nm, between 150 nm and 230 nm, between 200 nm and 230 nm, between 210 nm and 228 nm, between 218 nm and 226 nm, and/or between 220 nm and 224 nm. The use of a Far-UV light source, especially one at or around 222 nm, results in the generation of Far-UV light that has a relatively high energy (e.g., more energy than provided by a 254 nm UV-C light source) but is safe for use around humans. For example, the Far-UV light source does not penetrate the outer (non-living) layer of skin. However, because some pathogens (e.g., viruses and bacteria) are of micrometer or smaller dimensions, Far-UV light can penetrate and inactivate them. A Far-UV light source can also achieve full power more quickly and operate over a much broader temperature range than a 254 mn UV-C light source.

Certain aspects and features of the present disclosure relate to the safe and effective control of a Far-UV light source for environmental sanitization. The light source can be housed in any suitable housing. The light source can be battery-powered or mains-powered. The light source can be portable or fixed to an environment.

Examples of portable light sources include battery-powered or mains-powered lamps that can be brought into a room or other environment and set up for use. Examples of fixed light sources include lighting fixtures mounted on ceilings or other surfaces of rooms, vehicles, and the like. Fixed light sources can be mains-powered (e.g., a ceiling-mounted light fixture in a room that is powered by in-wall alternating current (AC) mains power) or battery-powered (e.g., a ceiling-mounted light fixture in a bus that is powered by direct current (DC) battery power).

The light source can be controlled by a controller. The controller can be or include a computing device (e.g., processor), simple logic device, or other suitable device (e.g., application-specific integrated circuit). The controller can run one or more algorithms for performing the various functions disclosed herein.

The light source can be controlled to automatically activate and deactivate as desired based on input data, including preset settings. Activation of the light source can be based on environment dimension information, environment expected usage information, light source specification information, regulatory compliance information, sensor data, expected remaining lifespan, and/or any combination thereof. Other inputs can also be used to activate the light source.

Environment dimension information can include any suitable information about the size of the environment in which the light source is being used. Environment dimension information can be user-provided or can be automatically determined by the system (e.g., via one or more sensors). Examples of environment dimension information include estimated areas and/or volumes of the environment, estimated distances from the light source to one or more surfaces within the environment, and other such information.

Environment expected usage information can be any suitable information about an expected usage of the environment. Examples of expected usage information include expected occupancy levels (e.g., overall and/or over time), expected duration of occupancies, expected rates and/or levels of pathogen entrance into the environment, expected rates of pathogen removal through techniques other than Far-UV sanitization, and other such information. Expected usage information can be provided directly and/or can be estimated from other information, such as received sensor data. For example, in some cases, received sensor data, such as from an occupancy sensor, can be used to generate and/or update expected usage information. In some cases, expected usage information can include expected future usage, such as estimated future times of expected occupancy. In such an example, a light source may be activated in advance of such an estimated future time so that it can be deactivated at the estimated future time, thus providing a sanitized environment for when occupancy is estimated.

Light source specification information can include any information about the light source itself, such as output frequency, power (e.g., voltage and/or current) requirements, driving specifications for different power output levels, expected lifespan, warranty information, or other such information.

Regulatory compliance information can include any information related to compliance with rules, laws, and/or guidelines. Examples of such rules, laws, and/or guidelines can include those promulgated by governments (e.g., federal or local laws or rules), corporations (e.g., building guidelines, lessor rules, or internal company rules), or other establishments (e.g., compliance and certification associations). Such rules, laws, and/or guidelines can be mandatory or optional.

Regulatory compliance information can include information about sanitization levels and/or procedures that should be reached and/or undertaken for the environment. For example, certain regulatory compliance information can include instructions to sanitize a space for at least a minimum number of minutes each day using a Far-UV light source. In some cases, regulatory compliance information can be dependent on the environmental dimension information, environment expected usage information, and/or light source specification information. For example, a minimum number of minutes each day (or other time period) can be based on the size of the environment (e.g., larger spaces may need longer periods of sanitization than smaller spaces), the expected use of the environment (e.g., spaces where individuals linger and/or may be in contact with more pathogens may need longer periods of sanitization than spaces where individuals pass through quickly or may have already been subject to some degree of sanitization), and/or the light source specification information (e.g., longer durations of sanitization may be needed for light sources with lower output power than those with higher output power).

Sensor data can include any data received from one or more sensors associated with the light source. For example, one or more occupancy sensors (e.g., motion sensors or other occupancy sensors) can indicate the presence of and/or number of individuals within the environment. Activation of the light source can be based, at least in part, on the sensor data. For example, activation of the light source can occur only or more often when the occupancy sensor indicates there are few or no individuals within the environment. In some cases, other sensor data can be received and used. Examples of other sensor data include sensor data about the environment (e.g., temperature, air quality, distances, illumination, sound, and the like) and/or sensor data about the light source (e.g., temperature, voltage, current, illumination, sound, and the like). Other sensor data can be used.

Expected remaining lifespan can include any information about the expected remaining time until the light source may fail (e.g., completely cease to output Far-UV light and/or cease to provide adequate output power for sanitization) and/or become inefficient (e.g., efficiency drops below a threshold value). Expected remaining lifespan can be based on received light source specification information (e.g., estimated total lifespan), actual light source usage (e.g., logged light source usage), sensor data (e.g., temperature, voltage, and/or current of the light source), or any combination thereof. In some cases, when the expected remaining lifespan drops below a threshold amount, a maintenance alert can be generated. The maintenance alert can indicate which light source needs to be replaced and when it may need to be replaced. In some cases, the maintenance alert can be used to suggest and/or automatically purchase replacement light sources.

In addition to controlling the light source, the controller can log usage of the light source. In some cases, this log can be used to update the expected remaining lifespan. In some cases, this log can be used to generate one or more reports of light source activation. In some cases, such a report can include a compliance report. A compliance report can be used to show and/or certify compliance with the laws, rules, and/or guidelines associated with the regulatory compliance information.

Certain aspects and features of the present disclosure are able to extend the life of the UV light source by minimizing usage of the light source to only times needed to achieve the desired sanitization. Thus, rather than keeping the light source on at all times or at all times when individuals are not present, the light source can be intelligently activated and deactivated as needed to achieve the desired level of sanitization, thus extending the length of time a single light source can be used in an environment before it must be replaced.

Certain aspects and features of the present disclosure are suitable to optimize the sanitization process, improve operational efficiency, reduce costs, and/or ensure regulatory compliance.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic side view of an environment 100 with two Far-UV sanitization devices 102, according to certain aspects of the present disclosure. The environment 100 of FIG. 1 is depicted as a conference room for illustrative purposes, although any other suitable environment can be used. The environment 100 includes pathogens 112, 114, 116. Pathogens 112 can be entrained in or otherwise suspended in air 110 within the environment 100. Pathogens 114 can be located on surfaces (e.g., a surface of table 122 or a surface of chair 124) of the environment 100. Pathogens 116 can be located on individuals 120 within the environment.

Sanitization device 102 are depicted as two light fixtures fixed to a ceiling of the environment 100. In some cases, however, sanitization devices can be located elsewhere in the environment 100, such as in the form of light fixtures fixed to the table 122, battery-powered light fixtures placed on the chair 124, or otherwise located within the environment. Each sanitization device 102 can include a light source 104 capable of outputting light rays 108 in the form of Far-UV light. The light rays 108 can contact pathogens 112, 114, 116 to kill, destroy, or otherwise render them unharmful to humans.

In some cases, each sanitization device 102 can include its own controller 106. Each sanitization device 102 can include a single light source 104 coupled to the controller 106. When multiple light sources 104 are needed, one or more controllers 106 can be used. For example, in some cases, multiple light sources 104, located in a common housing or separate housings, can be coupled to a single controller 106. In another example, multiple light sources 104 located in a common housing or separate housings, can each be coupled to a respective controller 106. In some cases, when multiple controllers 106 are used in a single environment, each controller 106 can operate independently. In other cases, however, when multiple controllers 106 are used in an single environment, one of the controllers 106 can operate as a leader controller and other controllers 106 can operate as follower controllers. The leader controller can issue instructions to follower controllers to activate the light sources 104 associated with each follower controller.

A controller 106 can be programmed using any suitable interface device. In some cases, a wired interface (not shown) can be coupled to the controller 106 to program the controller 106. In some cases, a computing device 126 (e.g., a computer, tablet, and/or smartphone) can be used to program and/or control controller 106. The computing device 126 can communicate directly with the controller 106, such as via a wired or wireless connection (e.g., Bluetooth, Wi-Fi, general radio frequency interfacing, or the like). In some cases, computing device 126 can communicate with the controller 106 indirectly, such as via a cloud 128. In such cases, controller 106 can communicate with a cloud 128 (e.g., via a local intranet or the Internet) to receive settings, information, and other controls.

In some cases, one or more sensors 130 can be associated with one or more controllers 106. The sensor(s) 130 can detect information about the environment 100, such as occupancy in the environment. In some cases, sensor 130 can be a motion sensor. In some cases, one or more sensors 130 can be incorporated into the same housing as the controller 106, although that need not always be the case.

In some cases, a single controller 106 can be used to control light sources 104 located in multiple environments 100. For example, a single controller 106 may control a first light source in a first environment using information associated with the first environment, and may also control a second light source in a second environment using information associated with the second environment.

Use of the sanitization device 102 as disclosed herein can cause some or all of the pathogens 112, 114, 116 to be rendered inert (e.g., killed or otherwise rendered unharmful to humans).

Figure 2:
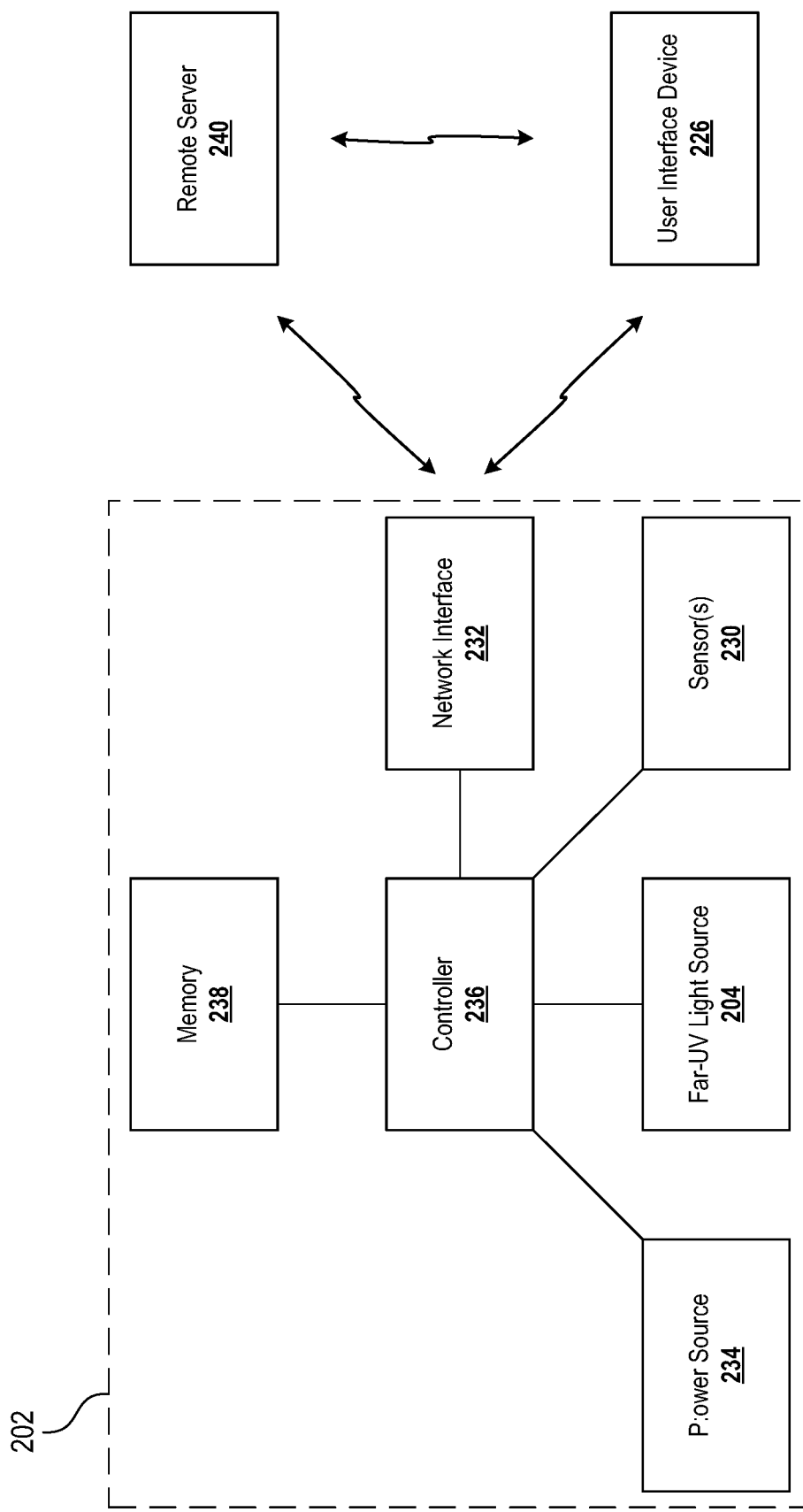
FIG. 2 is a schematic view of a Far-UV sanitization device, according to certain aspects of the present disclosure.

FIG. 2 is a schematic view of a Far-UV sanitization device 202, according to certain aspects of the present disclosure. The sanitization device 202 can be similar to the sanitization device 102 of FIG. 1. The sanitization device 202 can include any of the modules depicted in FIG. 2, as well as additional and/or fewer modules. Various groupings of modules depicted in FIG. 2 can be located in a single housing and/or separate housings.

Controller 236 can be primarily responsible for activating and deactivating the Far-UV light source 204. In some cases, controller 236 can be coupled to multiple light sources, as described herein.

The sanitization device 202 can include a power source 234 that provides power to the controller 236 and/or the Far-UV light source 204. In some cases, power source 234 can be a battery or similar portable power source (e.g., a high capacity capacitor). In some cases, power sources 234 can be a mains power source, such as a 120V or 230V AC power supply. In some cases, the power source 234 can convert incoming power (e.g., mains power) into appropriate output power (e.g., voltage and current) for different elements of the sanitization device 202.

The sanitization device 202 can include a memory 238. Memory 238 can store information associated with the operation of the light source 204. For example, memory 238 can store received information (e.g., information related to the environment and/or regulatory compliance, sensor data, and the like), current settings (e.g., time for and/or duration of next activation), and/or logs (e.g., logs of the time and/or duration of past activations). Memory 238 can also store information related to the operation of any processing and/or algorithms disclosed herein. Memory 238 can take the form of one or more memory devices (e.g., memory modules, storage drives, and the like) located in a single or separate housings. In some cases, some or all of memory 238 can be incorporated within controller 236.

The sanitization device 202 can include one or more sensors 230. Sensor 230 can be any suitable sensor, such as a distance sensor, a motion sensor, an infrared sensor, a camera, a light sensor (e.g., UV light sensor), a temperature sensor, an air quality sensor, a pathogen sensor, a current sensor, a voltage sensor, or the like. In some cases, the one or more sensors 230 include an imaging device, such as an optical camera or a thermal imager (e.g., thermal imaging sensor). In some cases, the imaging device can have a wide field of view (FOV), such as a field of view sufficient to obtain imaging data from an entire environment or a sufficient percentage of the environment to make a reliable determination of occupancy. For example, an imaging device with a wide field of view can be used in an elevator to ensure the entire elevator is unoccupied before beginning sanitization.

In some cases, the one or more sensors 230 includes a wide FOV optical camera having a field of view at or greater than 120°, 130°, 140°, 150°, 160°, 175°, or 180°. The wide FOV optical camera can have a field of view of 175° or within 5° of 175°. The wide FOV optical camera can obtain image data in the visible light spectrum. A wide FOV optical camera can be especially useful for capturing images of an environment (e.g., the inside of an elevator), which can then be compared to a baseline image (e.g., captured by the same FOV optical camera when the environment is unoccupied) to determine whether or not the environment is occupied.

In some cases, the one or more sensors 230 includes a wide FOV thermal imager having a field of view at or greater than 90°, 95°, 100°, 105°, or 110°. The wide FOV thermal imager can have a field of view of 110° or within 5° of 110°. The wide FOV thermal imager can obtain image data in the thermal spectrum (e.g., 1 to 14 µm, although other ranges can be used). In some cases, the wide FOV thermal imager can have a low resolution, such as at or below 128 pixels, 64 pixels, 32 pixels, 16 pixels, 8 pixels, or the like. A wide FOV thermal imager with a low resolution can be especially useful in locations where increased privacy is desired and/or optical cameras are undesirable or unusable (e.g., restrooms). In such cases, the wide FOV thermal imager can capture thermal data (e.g., thermal image data) that is indicative of whether or not the environment is occupied, without sufficient resolution to compromise privacy. The wide FOV thermal imager can capture thermal data and compare it to background thermal data or baseline thermal data to determine whether or not the environment is occupied.

A sensor 230 can be located on or within a housing shared by other elements of the sanitization device 202, such as the light source 204 or controller 236. In some cases, sensor 230 can be located within a separate housing.

The sanitization device 202 can include a network interface 232. The network interface 232 can be incorporated into controller 236 or be separate from controller 236. The network interface 232 can facilitate communications between the controller 236 and a remote server 240 and/or a user interface device 226 (e.g., computing device 126 of FIG. 1). The network interface 232 can be based on wired or wireless communication protocols. In some cases, the network interface 232 can further operate as a sensor to detect nearby wireless devices (e.g., Bluetooth devices). In such an example, the network interface 232 can operate as a sensor (e.g., sensor 230) to detect the presence of individuals in an environment by detecting the presence of wireless devices (e.g., cell phones, laptops, tablets, radiofrequency identification badges, and the like).

While depicted as separate devices in FIG. 2, in some cases, the user interface device 226 and/or remote server 240 can be part of sanitization device 202. Remote server 240 can be a computer server, such as an Internet-accessible, intranet-accessible, or cloud-based server that can provide data to or receive data from the controller 236. In some cases, a user interface device 226 can communicate with controller 236 directly (e.g., via a wired or wireless connection with network interface 232). In some cases, user interface device 226 can communicate with controller 236 via remote server 240.

Remove server 240 and/or user interface device 226 can be used to program and/or otherwise set up or operate the sanitization device 202.

Figure 3:
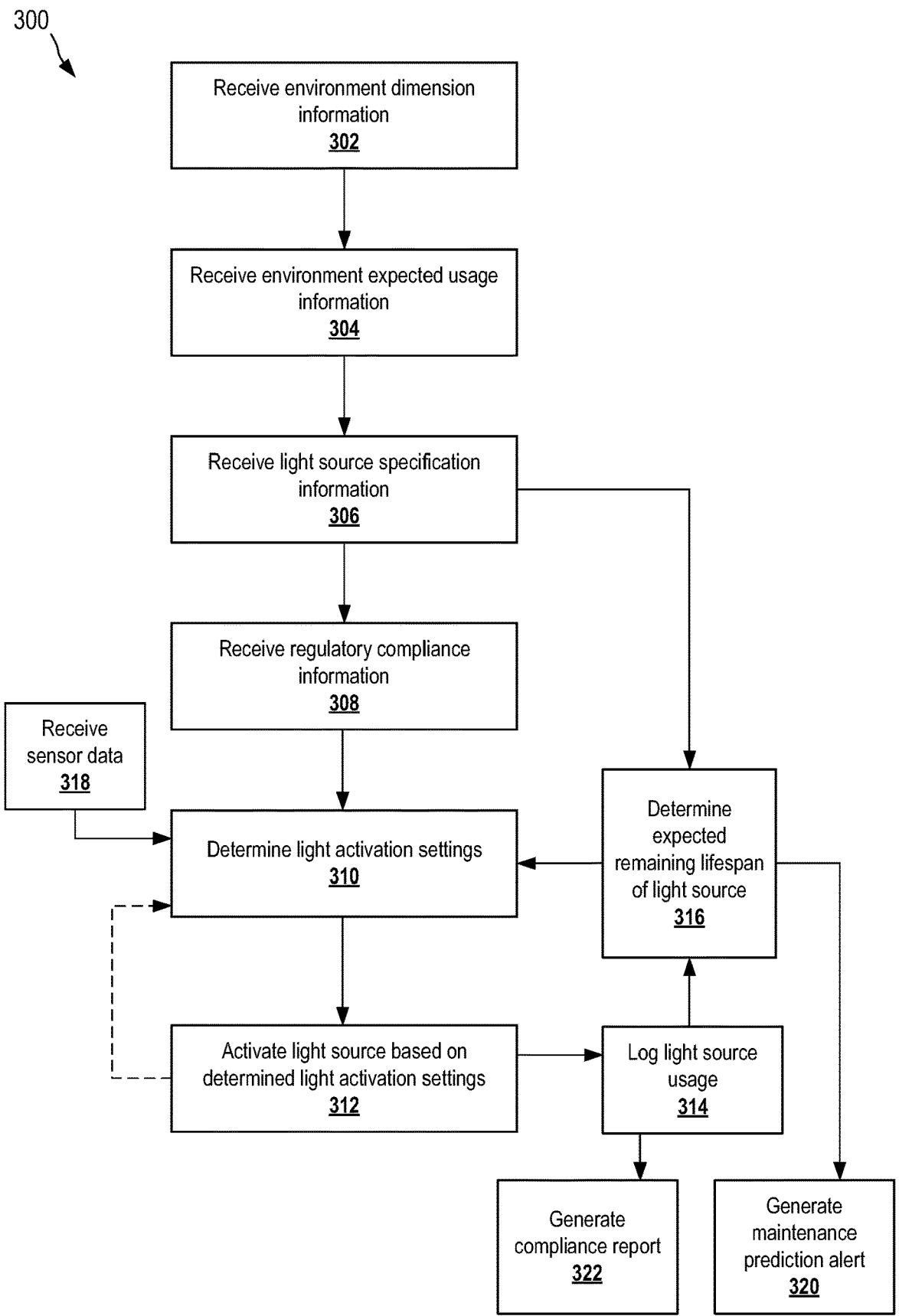
FIG. 3 is a flowchart depicting a process for using a Far-UV sanitization device, according to certain aspects of the present disclosure.

FIG. 3 is a flowchart depicting a process 300 for using a Far-UV sanitization device, according to certain aspects of the present disclosure. Process 300 can be performed using any suitable sanitization device, such as the sanitization devices 102, 202 of FIGS. 1 and 2, respectively. Process 300 can be performed by a controller of the sanitization device.

At block 302, environmental dimension information can be received.

At block 304, environmental expected usage information can be received.

At block 306, light source specification information can be received.

At block 308, regulatory compliance information can be received. In some cases, receiving regulatory compliance information at block 308 can include using the environmental dimension information, environmental expected usage information, and/or light source specification information to identify applicable regulatory compliance information. For example, the environmental dimension information, environmental expected usage information, and/or light source specification information can be used to look up applicable regulatory compliance information from a database accessible to the sanitization device.

At block 310, light activation settings can be determined. Determining light activation settings can be based on the environmental dimension information, the expected usage information, the light source specification information, the regulatory compliance information, or any combination thereof. The light activation settings can include settings related to when to activate the light source and for how long the light source should be activated.

In some cases, at block 318, sensor data can be received. Sensor data can include sensor data associated with the environment and/or sensor data associated with the light source. In some cases, determining light activation settings at block 310 can further be based on the received sensor data. In some cases, determining light activation settings at block 310 include triggering light activation upon receiving specified information from the sensor data (e.g., triggering upon receiving a signal indicating occupancy of the environment is below a threshold or at zero).

At block 312, the light source is activated based on the determined light activation settings from block 310. Activation the light source can involve supplying power to one or more light sources to generate Far-UV light within the environment. In some cases, activating the light source at block 312 can include keeping the light source active for a determined duration before deactivating the light source. In some cases, activating the light source at block 312 can include keeping he light source active until deactivating the light source in response to receiving a deactivation signal. The deactivation signal can be based on received sensor data from block 318.

In some cases, light source usage can be logged at block 314 in response to activating the light source at block 312. Logging light source usage at block 314 can include logging an activation time, duration, and/or deactivation time associated with the light source. In some cases, other information associated with the activation of the light source can be logged, such as settings determined at block 310 that are used to activate the light source at block 312. In some cases, logging light source usage at block 314 can include appending an existing log of light source usage. In some cases, process 300 can include receiving a signal indicative of replacement of the light source. In response to receiving such a signal, the log from block 314 can be erased, restarted, or replaced with a new log.

At block 316, an expected remaining lifespan of the light source 316 can be determined. The expected remaining lifespan can be determined based on the light source specification information from block 306 and/or the light source usage from block 314. In some cases, determining light activation settings at block 310 can further include using the determined expected remaining lifespan from block 316, such as to optimize remaining lifespan of the light source and/or to time expected failure of the light source for convenient times for replacement.

In some cases, a maintenance prediction alert can be generated at block 320. Generating the maintenance prediction alert can include generating an alert about a future anticipated need for maintenance (e.g., an expected date when the light source may need to be replaced or repaired). In some cases, generating the maintenance prediction alert can include generating an alert when an expected remaining lifespan of the light source as determined at block 316 drops below a threshold. In some cases, generating the maintenance prediction alert can be further based on the determined light activation settings 310. In some cases, generating the maintenance prediction alert can include providing an indication of the remaining lifespan of the light source and/or an indication of the remaining number of days of sanitization left. For example, for a light source with an estimated 50 hours of lifespan remaining, the light source may provide five (5) days of sanitization if used for approximately ten (10) hours per day.

In some cases, after activation (and optionally subsequent deactivation) of the light source at block 312, the process 300 can continue with determining further light activation settings at block 310. Determining such further light activation settings can be based on past information and/or data received at blocks 302, 304, 306, 308, 318, 316, and/or new information and/or data received at new instances of blocks 302, 304, 306, 308, 318, 316.

In some cases, a compliance report can be generated at block 322. The compliance report can be generated based on logged light source usage at block 314. In some cases, the compliance report can be further based on any other information associated with activation of the light source, such as regulatory compliance information received at block 308 and light activation settings from block 310.

In some cases, blocks of process 300 can be removed, replaced, added, or moved around, as appropriate. For example, in some cases expected usage information is not used and block 304 can be removed. In another example, determining an expected remaining lifespan at block 316 occurs prior to determining light activation settings at block 310. Other arrangements of blocks can occur.

Figure 4:
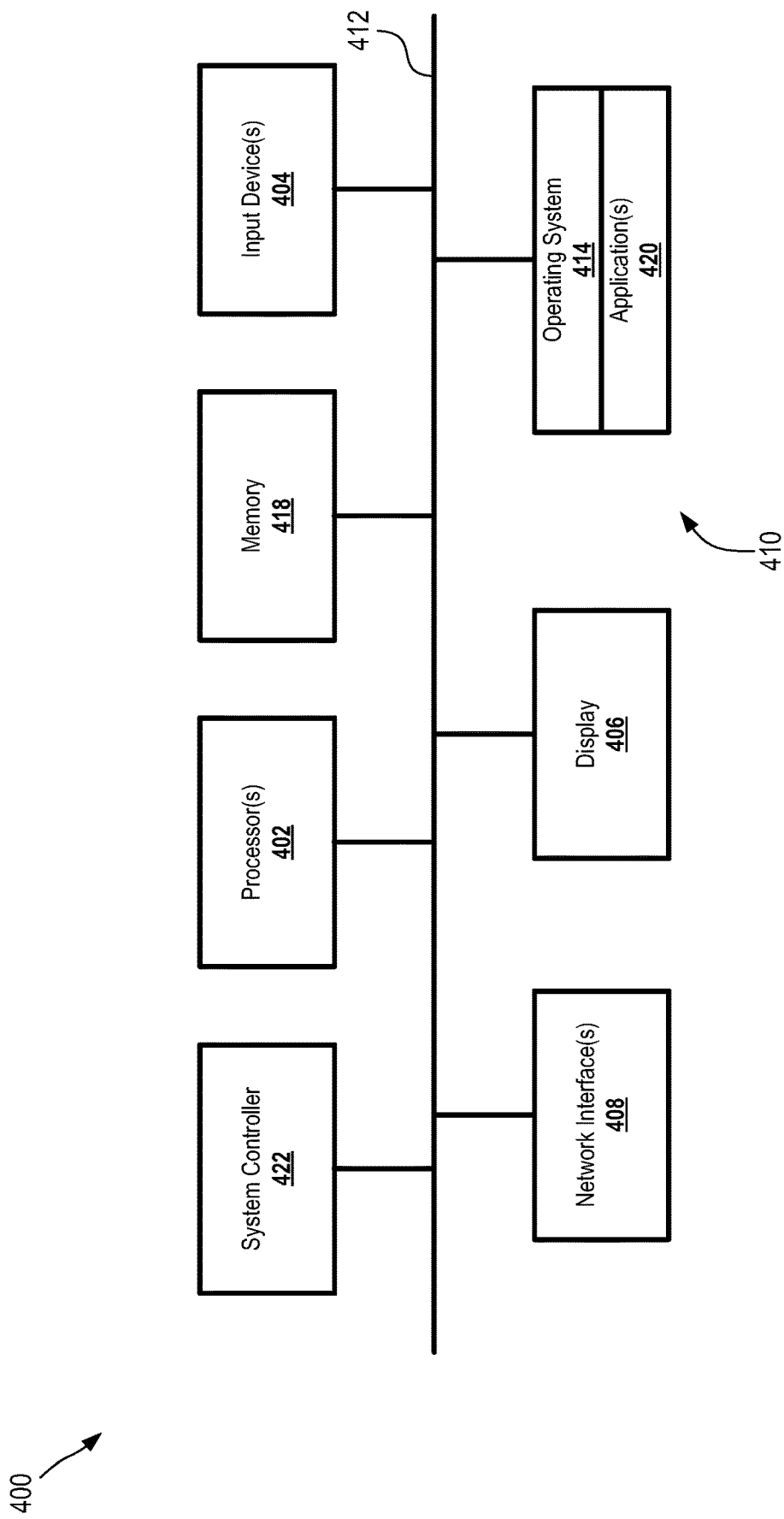
FIG. 4 is a block diagram depicting an example system architecture for implementing certain features and processes of the present disclosure.

FIG. 4 is a block diagram of an example system architecture 400 for implementing features and processes of the present disclosure, such as those presented with reference to FIGS. 1-3. The architecture 400 can be used to implement any suitable computing device (e.g., a server, workstation, tablet, or other such device) for practicing the various features and processes of the present disclosure. The architecture 400 can be implemented on any electronic device that runs software applications derived from compiled instructions, including without limitation personal computers, servers, smart phones, electronic tablets, game consoles, email devices, and the like. In some implementations, the architecture 400 can include one or more processors 402, one or more input devices 404, one or more display devices 406, one or more network interfaces 408, and one or more computer-readable mediums 410. Each of these components can be coupled by bus 412.

In some cases, system architecture 400 can be incorporated into a light fixture, such as light fixture design of the Far-UV sanitization device 102 of FIG. 1. In some cases, system architecture 400 can be incorporated into a computing device, such as interface device 126 of FIG. 1. In some cases, system architecture 400 can be incorporated into a remote server, such as remote server 240 of FIG. 2, which can facilitate performance of one or more aspects of the present disclosure, such as those disclosed herein.

In some implementations, system architecture 400 can correspond to a single server in a rack of servers. Various rack configurations can be implemented. For example, a rack can include multiple chassis and each chassis can contain multiple servers. Each server in the rack can be connected by various hardware components (e.g., backbone, middle plane, etc.).

Display device 406 can be any known display technology, including but not limited to display devices using Liquid Crystal Display (LCD) or Light Emitting Diode (LED) technology. Processor(s) 402 can use any known processor technology, including but not limited to graphics processors and multi-core processors. Input device 404 can be any known input device technology, including but not limited to a keyboard (including a virtual keyboard), mouse, track ball, and touch-sensitive pad or display. Bus 412 can be any known internal or external bus technology, including but not limited to ISA, EISA, PCI, PCI Express, NuBus, USB, Serial ATA or FireWire.

Computer-readable medium 410 can be any medium that participates in providing instructions to processor(s) 402 for execution, including without limitation, non-volatile storage media (e.g., optical disks, magnetic disks, flash drives, etc.) or volatile media (e.g., SDRAM, ROM, etc.). The computer-readable medium (e.g., storage devices, mediums, and memories) can include, for example, a cable or wireless signal containing a bit stream and the like. However, when mentioned, non-transitory computer-readable storage media expressly exclude media such as energy, carrier signals, electromagnetic waves, and signals per se.

Computer-readable medium 410 can include various instructions for implementing operating system 414 and applications 420 such as computer programs. The operating system can be multi-user, multiprocessing, multitasking, multithreading, real-time and the like. The operating system 414 performs basic tasks, including but not limited to: recognizing input from input device 404; sending output to display device 406; keeping track of files and directories on computer-readable medium 410; controlling peripheral devices (e.g., disk drives, printers, etc.) which can be controlled directly or through an I/O controller; and managing traffic on bus 412. Computer-readable medium 410 can include various instructions for implementing firmware processes, such as a BIOS. Computer-readable medium 410 can include various instructions for implementing any of processes described herein, including at least process 300 of FIG. 3.

Memory 418 can include high-speed random access memory and/or non-volatile memory, such as one or more magnetic disk storage devices, one or more optical storage devices, and/or flash memory (e.g., NAND, NOR). The memory 418 (e.g., computer-readable storage devices, mediums, and memories) can include a cable or wireless signal containing a bit stream and the like. However, when mentioned, non-transitory computer-readable storage media expressly exclude media such as energy, carrier signals, electromagnetic waves, and signals per se. The memory 418 can store an operating system, such as Darwin, RTXC, LINUX, UNIX, OS X, WINDOWS, or an embedded operating system such as VxWorks.

System controller 422 can be a service processor that operates independently of processor 402. In some implementations, system controller 422 can be a baseboard management controller (BMC). For example, a BMC is a specialized service processor that monitors the physical state of a computer, network server, or other hardware device using sensors and communicating with the system administrator through an independent connection. The BMC is configured on the motherboard or main circuit board of the device to be monitored. The sensors of a BMC can measure internal physical variables such as temperature, humidity, power-supply voltage, fan speeds, communications parameters and operating system (OS) functions.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computing system that includes a back-end component, such as a data server, or that includes a middleware component, such as an application server or an Internet server, or that includes a front-end component, such as a client computer having a graphical user interface or an Internet browser, or any combination thereof. The components of the system can be connected by any form or medium of digital data communication such as a communication network. Examples of communication networks include, e.g., a LAN, a WAN, and the computers and networks forming the Internet.

The computing system can include clients and servers. A client and server are generally remote from each other and typically interact through a network. The relationship of client and server arises by virtue of computer programs running on the respective computers and having a client-server relationship to each other.

One or more features or steps of the disclosed embodiments can be implemented using an application programming interface (API). An API can define one or more parameters that are passed between a calling application and other software code (e.g., an operating system, library routine, function) that provides a service, that provides data, or that performs an operation or a computation.

The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API.

In some implementations, an API call can report to an application the capabilities of a device running the application, such as input capability, output capability, processing capability, power capability, communications capability, and the like.

Figure 5:
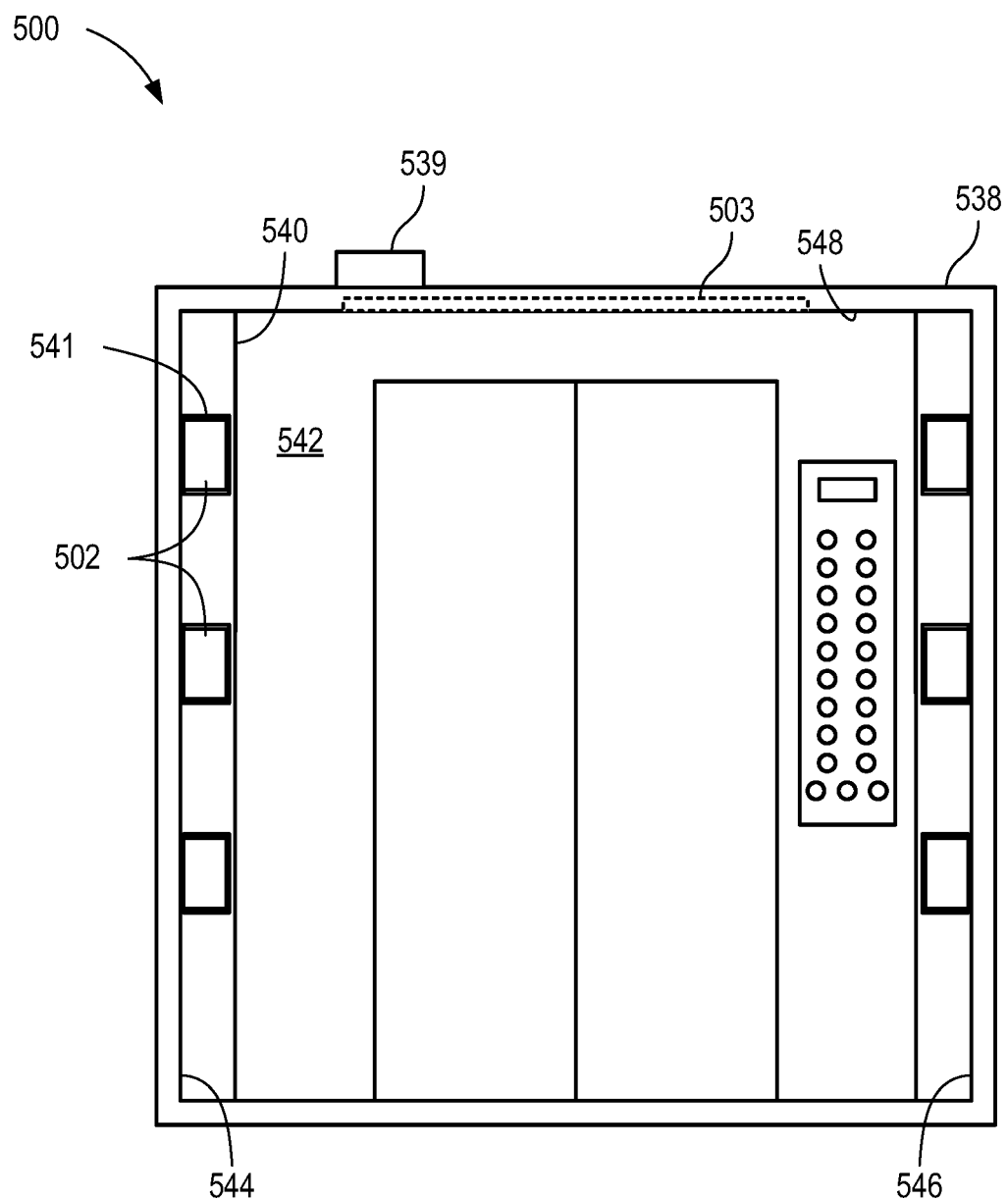
FIG. 5 is a front view of a Far-UV sanitization system within an elevator, according to certain aspects of the present disclosure.

FIG. 5 is a front view of a Far-UV sanitization system 500 within an elevator 538, according to certain aspects of the present disclosure. The Far-UV sanitization system 500 can include a number of Far-UV sanitization devices 502, 503. While depicted with reference to an elevator 538, the Far-UV sanitization system 500 can be used in any suitable environment, such as enclosed environments. Far-UV sanitization devices 502, 503 can be any suitable Far-UV sanitization device, such as Far-UV sanitization device 202 of FIG. 2.

The elevator 538 can include walls 542, 544, 546, a floor, and a ceiling 548, although that need not always be the case. For example, in some cases, an elevator 538 can include one or more round (e.g., circular) walls.

In some cases, the Far-UV sanitization system 500 can include a set of Far-UV sanitization device 502 that are positioned along walls 542, 544, 546 of the elevator 538. In some cases, the Far-UV sanitization devices 502 are mounted to one or more walls 542, 544, 546 of the elevator 538, although that need not always be the case. In some cases, the Far-UV sanitization devices 502 can be mounted to the ceiling 548 or floor of the elevator 538, or otherwise mounted to be positioned adjacent a wall 542, 544, 546 of the elevator 538.

In some cases, a frame 540 can be used around one or more of the Far-UV sanitization devices 502. In some cases, one or more Far-UV sanitization devices 502 can be mounted to a frame 540, although that need not always be the case. The frame 540 can help secure the Far-UV sanitization devices 502 in the elevator 538 in desired locations (e.g., to provide a desired level of coverage within the elevator 538) while also providing a complementary aesthetic to the elevator 538. For example, in an elevator with dark wood paneling on walls 542, 544, 546, the frame 540 can be treated to look like the same dark wood material to provide an unobtrusive and aesthetically pleasing addition to the elevator 538, although that need not always be the case. In some cases, the frame 540 is made of a fabricated metal (e.g., stainless steel, aluminum, bronze, or the like). In some cases, the frame 540 can include hooks or other attachment devices to facilitate attaching the frame 540 to common elevator hardware, such as to mounting rails or cleats of the elevator or to existing panels. The frame 540 can be removable for maintenance and replacement of lamps in the Far-UV sanitization devices 502. The frame 540 can be shaped and otherwise configured to be tamper resistant.

The frame 540 can include a window 541 for each Far-UV sanitization device 502, through which Far-UV light can pass. In some cases, window 541 can be covered by a lens that is transparent or translucent (e.g., at least 90%, 95%, 98%, 99%, 99.5%, 99.9% transmittance) to the wavelength (s) produced by the Far-UV sanitization device 502 (e.g., a quartz lens). In some cases, window 541 can include a movable panel or other covering that occludes the Far-UV sanitization device 502 when it is not sanitizing and automatically opens to no longer occlude the Far-UV sanitization device 502 when sanitization is occurring or imminent. In some cases, frame 540 can be shaped to attach to adjacent walls (e.g., wall 542 and wall 544, or wall 542 and wall 546). In some cases, frame 540 attaches to form a 45° angle between the adjacent walls, although other angles or shapes (e.g., rounded, curvilinear, circular, and the like) can be used. Frame 540 can provide protection to the Far-UV sanitization device 502 and can resist tampering. In some cases, frame 540 can be a tamper-proof design. In some cases, frame 540 can be integral with one or more panels of the adjacent walls.

While sets of Far-UV sanitization devices 502 are depicted at each corner of the elevator 538, that need not always be the case. Additionally, while three Far-UV sanitization devices 502 are depicted at each corner of the elevator 538 in a spaced apart, stacked fashion, that need not always be the case. In some cases, one or more long, continuous Far-UV sanitization devices can be used. Any number of Far-UV sanitization devices can be used at a corner.

In some optional cases, a Far-UV sanitization device 503 can be positioned at the ceiling 548 (e.g., on, within, or above the ceiling 548). The Far-UV sanitization device 503 can direct UV light rays downwards, into the elevator 538. Any number of Far-UV sanitization devices 503 can be used, in any suitable pattern and of any suitable size.

In some cases, each of the Far-UV sanitization devices 502, 503 can be replaced with a Far-UV light source, in which case the other components of a Far-UV sanitization device (e.g., memory, controller, network interface, sensor, and the like) can be located in other locations, such as in an optional control box 539. The control box 539 can be located above the elevator 538, or in any other suitable location.

In some cases, the Far-UV sanitization system 500 can include or can operatively couple to the elevator's control system. In such cases, the Far-UV sanitization system 500 may be able to make use of information from the elevator's control system, such as elevator occupancy (e.g., to detect when the elevator is not occupied and/or ascertain occupancy patterns), elevator door position (e.g., open or closed), and notification of an elevator call (e.g., so the Far-UV sanitization system 500 can stop illuminating as the elevator 538 approaches the floor to which it was called).

In some cases, Far-UV sanitization devices can be mounted on or within the elevator doors. In some cases, opening of the elevator doors can automatically cause such Far-UV sanitization devices to be hidden behind the wall 542 of the elevator 538.

Figure 6:
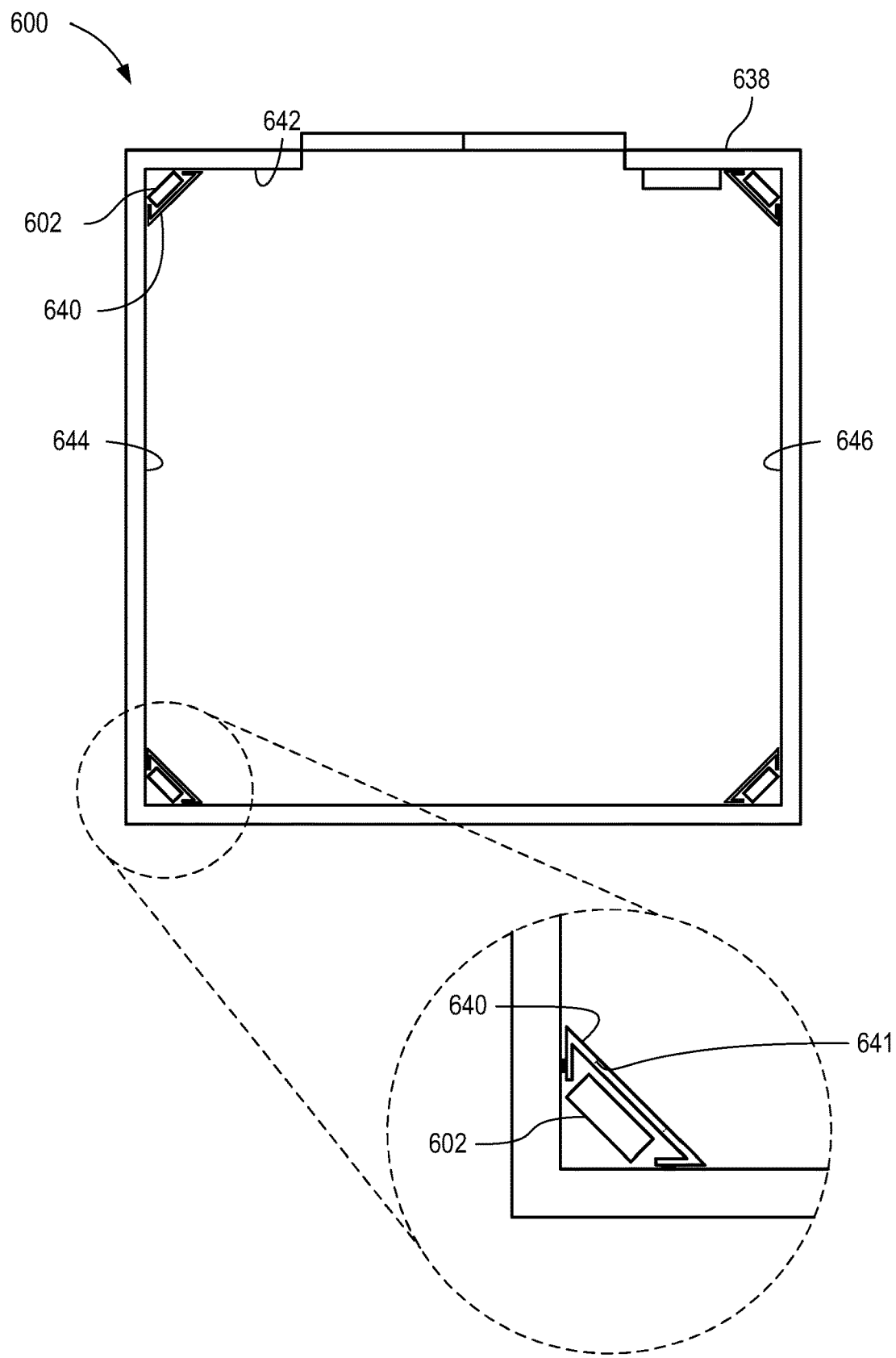
FIG. 6 is a combination top view and enlarged view of a Far-UV sanitization system within an elevator, according to certain aspects of the present disclosure.

FIG. 6 is a combination top view and enlarged view of a Far-UV sanitization system 600 within an elevator 638, according to certain aspects of the present disclosure. The Far-UV sanitization system 600 can be Far-UV sanitization system 500 of FIG. 5.

As depicted in FIG. 6, the Far-UV sanitization system 600 includes four sets of Far-UV sanitization devices 602, with each set being located at a corner between adjacent walls 642, 646, 648. In the top view, the Far-UV sanitization device 602 is seen positioned behind frame 640. In some cases, one or more Far-UV sanitization devices 602 can be coupled to a frame 640, although that need not always be the case. In some cases, one or more Far-UV sanitization devices 602 can be coupled to the elevator via frame 640. Frame 640 can be attached to the elevator 638 in any suitable fashion, such as to adjacent walls. Each frame 640 can include a window 641 for each Far-UV sanitization device 602.

Figure 7:
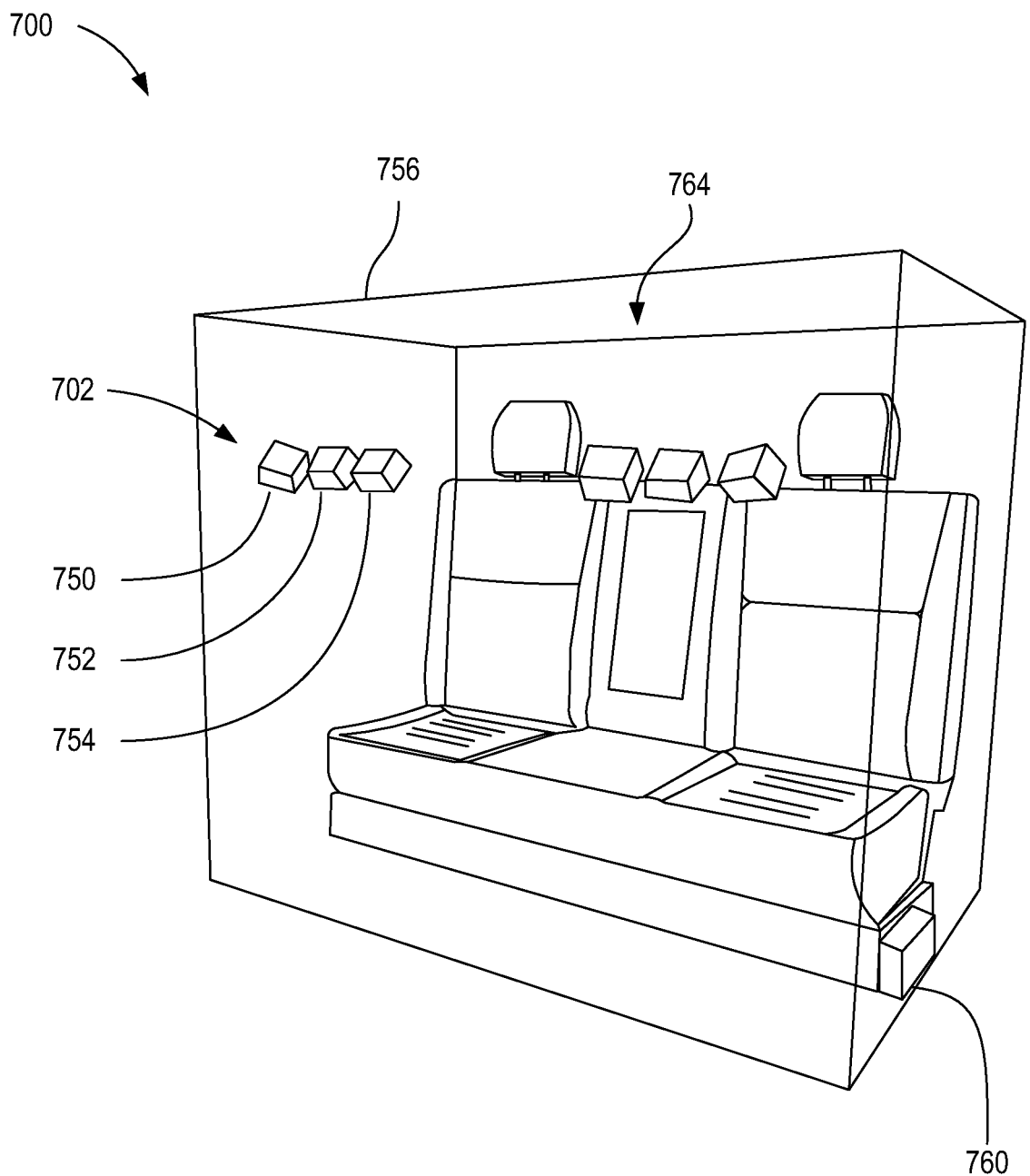
FIG. 7 is an axonometric diagram depicting a Far-UV sanitization system for sanitizing a vehicle surface, according to certain aspects of the present disclosure.

FIG. 7 is an axonometric diagram depicting a Far-UV sanitization system 700 for sanitizing vehicle surfaces, according to certain aspects of the present disclosure. The Far-UV sanitization system 700 can include a number of Far-UV sanitization devices 702. The Far-UV sanitization system 700 can be used with any suitable vehicle surface, especially including surfaces of a vehicle interior 756. The Far-UV sanitization system 700 can be used with any suitable vehicle, such as a car, a truck, a bus, a boat, an airplane, a helicopter, or any other passenger vehicle. In some cases, the Far-UV sanitization system 700 can be set up to only sanitize a passenger compartment within a vehicle (e.g., the rear seats of a taxicab sedan or a cabin of an airplane), although that need not always be the case. In some cases, one or more Far-UV sanitization devices 702 can be positioned to illuminate high-contact area of a vehicle interior 756, such as vehicle seats 864. The Far-UV sanitization device can be positioned in any suitable location. In some cases, the Far-UV sanitization device 702 can be positioned spaced apart from a vehicle seat 764 and facing towards the vehicle seat 764. Far-UV sanitization device 702 can be any suitable Far-UV sanitization device, such as Far-UV sanitization device 202 of FIG. 2.

As depicted in FIG. 7, each Far-UV sanitization device 702 includes three light sources 750, 752, 754. Each of the light sources 750, 752, 754 can be oriented in different positions to cover different regions of the vehicle seat 756. In some cases, however, a Far-UV sanitization device 702 can include a single light source, two light sources, or more than three light sources.

In some cases, each of the Far-UV sanitization devices 702 can be replaced with one or more Far-UV light sources, in which case the other components of a Far-UV sanitization device (e.g., memory, controller, network interface, sensor, and the like) can be located in other locations, such as in an optional control box 760. The control box 760 can be located in any suitable location, such as adjacent a vehicle seat 756.

Far-UV sanitization devices 702 can be mounted to the vehicle in any suitable fashion, such as to a ceiling, floor, or wall of the vehicle, as well as to any other vehicle fixture (e.g., a seatback, headrest, partition, dashboard, or the like).

While described as being used to sanitize a vehicle interior 756, Far-UV sanitization devices 702 can be used to sanitize any surface of a vehicle, such as a trunk, a truck bed, a cargo area, or the like. In some cases, a Far-UV sanitization device can be used to sanitize an exterior surface of a vehicle, such as a door handle or an exterior truck bed.

Figure 8:
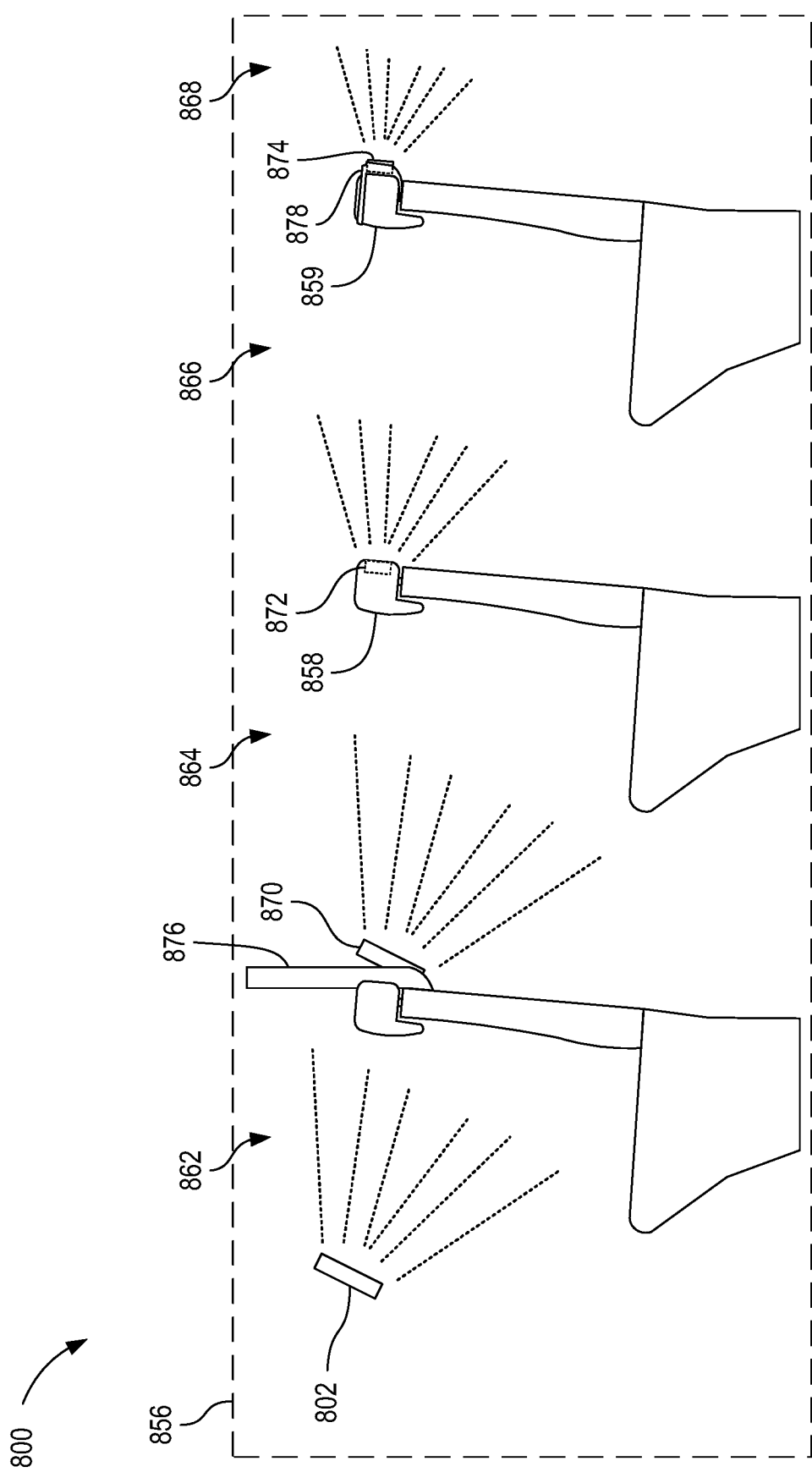
FIG. 8 is a schematic side view of a Far-UV sanitization system for sanitizing a vehicle surface, according to certain aspects of the present disclosure.

FIG. 8 is a schematic side view of a Far-UV sanitization system 800 for sanitizing a vehicle surface, according to certain aspects of the present disclosure. Far-UV sanitization system 800 can be similar to Far-UV sanitization system 700 of FIG. 7. For illustrative purposes, Far-UV sanitization system 800 is shown with four different Far-UV sanitization devices 802, 870, 872, 874 within a vehicle interior 856 used respectively to sanitize surfaces within a first region 862 (e.g., a first seat), a second region 864 (e.g., a second seat), a third region 866 (e.g., a third seat), and a fourth region 868 (e.g., a cargo space). However, a Far-UV sanitization system 800 may have any combination of any number of such Far-UV sanitization devices 802, 870, 872, 874 and can be used to sanitize vehicle surfaces in a vehicle having any number of regions and any number of vehicle seats.

Far-UV sanitization device 802 can be mounted on any suitable fixture within the vehicle, such as mounted from the floor, the ceiling, a dashboard, or the like. Far-UV sanitization device 802 can be positioned to illuminate the vehicle seat in the first region 862 with Far-UV light rays to sanitize surfaces in the first region 862.

Far-UV sanitization device 870 is mounted to a partition 876 between the first region 862 and the second region 864. For example, the partition 876 can be coupled to the vehicle seat of the first region 862. The Far-UV sanitization device 870 can be mounted to a surface of the partition 876 facing the vehicle seat in the second region 864, or can be otherwise mounted, such as mounted within the partition 876 or mounted to a far surface of the partition 876 (e.g., the surface facing away from the vehicle seat in the second region 864) with the partition 876 being transparent or translucent to Far-UV light rays or otherwise having an window or opening permitting Far-UV light rays to pass therethrough. Far-UV sanitization device 870 is positioned to illuminate the vehicle seat in the second region 864 with Far-UV light rays to sanitize surfaces in the second region 864.

In some cases, Far-UV sanitization device 870 can be positioned to not illuminate much or any of the first region 862 with Far-UV light rays. Such positioning can be useful, such as when used in a for-hire vehicle in which a driver located in the first region 862 remains in the vehicle seat while wanting to sanitize surfaces in the second region 864 between passengers.

Far-UV sanitization device 872 is mounted to a headrest 858 of the vehicle seat in the second region 864. The Far-UV sanitization device 872 can be mounted to a surface of the headrest 858 or can be mounted within the headrest 858 (e.g., recessed within). Far-UV sanitization device 872 is positioned to illuminate the vehicle seat in the third region 866 with Far-UV light rays to sanitize surfaces in the third region 866. In some cases, headrest 858 can be made and/or sold as a replacement to an existing headrest. In such cases, a user may remove the existing headrest (e.g., a factory-installed headrest) to replace it with the headrest 858 including the Far-UV sanitization device 872. The Far-UV sanitization device 872 can be electrically coupled to the electrical system of the vehicle, although that need not always be the case.

Far-UV sanitization device 874 is incorporated into a covering 878 that can be removably placed over an existing headrest 859. Far-UV sanitization device 874 can be positioned to illuminate surfaces in the fourth region 868, such as surfaces of a cargo area of the vehicle interior 856. Covering 878 permits a Far-UV sanitization device 874 to be retro-fit onto existing headrests 859 without needing to replace the existing headrest 859.

In some cases, Far-UV sanitization system 800 can include or be coupled to a system associated with operation of the vehicle (e.g., a control system of the vehicle or a smartphone app associated with operation of the vehicle, such as a ride-for-hire app). In such cases, the Far-UV sanitization system 800 may receive information from the other system to help control or improve operation of the Far-UV sanitization system 800. In an example, an occupancy sensor in the vehicle can be used to determine whether or not to sanitize the vehicle seat. In another example, a signal from an app (e.g., a ride-for-hire smartphone app) associated with the vehicle can indicate the end of a ride, in which case the Far-UV sanitization system 800 can automatically sanitize the passenger areas of the vehicle (e.g., second region 864). In such an example, automatic sanitization can occur immediately, after a predetermined delay, or upon detecting the opening and closing of doors. In some cases, the Far-UV sanitization system 800 can be manually triggered, such as via remote control, a remote signal from a computing device, or manual triggering of a switch, button, or the like.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the invention. Thus, the breadth and scope of the present invention should not be limited by any of the above described embodiments.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

As used below, any reference to a series of examples is to be understood as a reference to each of those examples disjunctively (e.g., "Examples 1-4" is to be understood as "Examples 1, 2, 3, or 4").

Example 1 is a method comprising: receiving environmental dimension information associated with an environment; receiving environmental expected usage information associated with the environment; receiving light source specification information associated with a light source in the environment, the light source operable to generate Far- UV light; receiving regulatory compliance information associated with the environment; determining light activation settings for activating the light source based on the environmental dimension information, the environmental expected usage information, the light source specification information, and the regulatory compliance information; and activating the light source based on the determined light activation settings.

Example 2 is the method of example(s) 1, further comprising receiving sensor data, wherein determining the light activation settings is further based on the sensor data.

Example 3 is the method of example(s) 2, wherein the sensor data includes environmental data associated with the environment.

Example 4 is the method of example(s) 3, wherein receiving the environmental dimension information includes: extracting one or more measurements from the environmental data; and calculating, using the one or more measurements, i) an estimated area within the environment; ii) an estimated volume within the environment; iii) an estimated distance between the light source and a surface within the environment; or iv) any combination of i-iii.

Example 5 is the method of example(s) 3 or 4, wherein the sensor data includes occupancy data associated with the environment, and wherein the expected usage information includes the occupancy data.

Example 6 is the method of example(s) 2-5, wherein the sensor data includes light source data associated with the light source.

Example 7 is the method of example(s) 6, wherein the light source data includes i) a detected frequency of the light source; ii) a detected power usage of the light source; iii) a detected level of output of the light source; iv) a temperature of the light source; or v) any combination of i-iv.

Example 8 is the method of example(s) 1-7, wherein receiving regulatory compliance information includes accessing the regulatory compliance information using i) the environmental dimension information, ii) the environmental expected usage information, iii) the light source specification information; or iv) any combination of i-iii.

Example 9 is the method of example(s)s 1-8, further comprising logging the activation of the light source.

Example 10 is the method of example(s) 9, further comprising generating a compliance report based on the logged activation of the light source and the received regulatory compliance information.

Example 11 is the method of example(s)s 1-10, further comprising determining an expected remaining lifespan of the light source, wherein determining the light activation settings is further based on the determined expected remaining lifespan of the light source.

Example 12 is the method of example(s) 11, further comprising generating a maintenance prediction alert associated with the light source, wherein generating the maintenance prediction alert is based on the determined expected remaining lifespan of the light source.

Example 13 is the method of example(s) 1-12, wherein the expected usage information includes i) an expected occupancy level per period of time; ii) a maximum occupancy level; iii) an expected duration per occupancy; iv) an expected rate of pathogen entrance into the environment; v) an expected rate of pathogen removal from the environment; or vi) any combination of i-v.

Example 14 is the method of example(s) 1-13, wherein activating the light source includes automatically moving a covering from a first position occluding the light source to a second position not-occluding the light source.

Example 15 is the method of example(s) 1-14, wherein activating the light source further includes activating an additional light source, wherein one of the light source and the additional light source is located on a ceiling and the other of the light source and the additional light source is located on a wall.

Example 16 is the method of example(s) 1-13, wherein the Far-UV light source has a frequency between 218 nm and 226 nm.

Example 17 is a system comprising: a control system including one or more processors; and a memory having stored thereon machine readable instructions; wherein the control system is coupled to the memory, and the method of any one of example(s)s 1-16 is implemented when the machine executable instructions in the memory are executed by at least one of the one or more processors of the control system.

Example 18 is a system for sanitizing an environment, the system including a control system configured to implement the method of any one of example(s)s 1-16.

Example 19 is a computer program product comprising instructions which, when executed by a computer, cause the computer to carry out the method of any one of example(s)s 1 to 16.

Example 20 is the computer program product of example(s) 19, wherein the computer program product is a non-transitory computer readable medium.

What is claimed is:

1. A method for automatically sanitizing a space, the method comprising:
   providing a light source operable to generate Far-UV light within an environment;
   providing a controller coupled to the light source to control operation of the light source;
   receiving, by the controller, environmental dimension information associated with the environment;
   receiving, by the controller, environmental expected usage information associated with the environment;
   receiving, by the controller, light source specification information associated with the light source;
   receiving, by the controller, regulatory compliance information associated with the environment;
   automatically determining, by the controller, light activation settings for activating the light source based on the environmental dimension information, the environmental expected usage information, the light source specification information, and the regulatory compliance information;
   receiving, by the controller, occupancy sensor data associated with the environment;
   determining that the environment is not occupied based on the received occupancy sensor data; and
   automatically activating the light source based on the determined light activation settings in response to determining that the environment is not occupied.

2. The method of claim 1, further comprising receiving sensor data, wherein determining the light activation settings is further based on the sensor data.

3. The method of claim 2, wherein the sensor data includes environmental data associated with the environment.

4. The method of claim 3, wherein receiving the environmental dimension information includes:
   extracting one or more measurements from the environmental data; and
   calculating, using the one or more measurements, i) an estimated area within the environment; ii) an estimated volume within the environment; iii) an estimated distance between the light source and a surface within the environment; or iv) any combination of i-iii.

5. The method of claim 2, wherein the sensor data includes light source data associated with the light source.

6. The method of claim 5, wherein the light source data includes i) a detected frequency of the light source; ii) a detected power usage of the light source; iii) a detected level of output of the light source; iv) a temperature of the light source; or v) any combination of i-iv.

7. The method of claim 1, wherein receiving regulatory compliance information includes accessing the regulatory compliance information using i) the environmental dimension information, ii) the environmental expected usage information, iii) the light source specification information; or iv) any combination of i-iii.

8. The method of claim 1, further comprising logging the activation of the light source in response to automatically activating the light source.

9. The method of claim 8, further comprising generating a compliance report based on the logged activation of the light source and the received regulatory compliance information.

10. The method of claim 1, further comprising determining an expected remaining lifespan of the light source, wherein determining the light activation settings is further based on the determined expected remaining lifespan of the light source.

11. The method of claim 1, further comprising:
logging light source usage in response to automatically activating the light source;
determining an expected remaining lifespan of the light source based on the light source specification information and the logged light source usage; and
generating a maintenance prediction alert associated with the light source, wherein generating the maintenance prediction alert is based on the determined expected remaining lifespan of the light source.

12. The method of claim 1, wherein activating the light source includes automatically moving a covering from a first position occluding the light source to a second position not-occluding the light source.

13. The method of claim 1, wherein activating the light source further includes activating an additional light source, wherein one of the light source and the additional light source is located on a ceiling and the other of the light source and the additional light source is located on a wall.

14. The method of claim 1, wherein the Far-UV light source has a frequency between 218 nm and 226 nm.

15. A non-transitory computer readable medium comprising instructions which, when executed by a computer, cause the computer to:
receive environmental dimension information associated with an environment;
receive environmental expected usage information associated with the environment;
receive light source specification information associated with a light source operable to generate Far-UV light within the environment;
receive regulatory compliance information associated with the environment;
automatically determine light activation settings for activating the light source based on the environmental dimension information, the environmental expected usage information, the light source specification information, and the regulatory compliance information;
receive occupancy sensor data associated with the environment;
determine that the environment is not occupied based on the received occupancy sensor data; and
automatically activate the light source based on the determined light activation settings in response to determining that the environment is not occupied.

16. A system for automatically sanitizing a space, the system comprising:
a light source operable to generate Far-UV light within an environment;
an occupancy sensor operable to determine occupancy of the environment;
a controller coupled to the occupancy sensor and the light source to control operation of the light source, the controller programmed to:
receive environmental dimension information associated with the environment;
receive environmental expected usage information associated with the environment;
receive light source specification information associated with the light source;
receive regulatory compliance information associated with the environment; and
automatically determine light activation settings for activating the light source based on the environmental dimension information, the environmental expected usage information, the light source specification information, and the regulatory compliance information;
receive occupancy sensor data associated with the environment from the occupancy sensor;
determine that the environment is not occupied based on the received occupancy sensor data; and
automatically activate the light source based on the determined light activation settings in response to determining that the environment is not occupied.

17. The system of claim 9, wherein the controller is further operable to generate a compliance report based on the logged activation of the light source and the received regulatory compliance information.

18. The system of claim 16, further comprising a moveable covering in proximity to the light source, wherein activating the light source includes automatically moving the covering from a first position occluding the light source to a second position not-occluding the light source.

19. The system of claim 16, further comprising an additional light source activated by the controller, wherein one of the light source and the additional light source is located on a ceiling and the other of the light source and the additional light source is located on a wall of the environment.

20. The system of claim 16, wherein the Far-UV light source has a frequency between 218 nm and 226 nm.

* * * * *